US008242293B2

(12) United States Patent
Gruter et al.

(10) Patent No.: US 8,242,293 B2
(45) Date of Patent: Aug. 14, 2012

(54) METHOD FOR THE SYNTHESIS OF ORGANIC ACID ESTERS OF 5-HYDROXYMETHYLFURFURAL AND THEIR USE

(75) Inventors: Gerardus Johannes Maria Gruter, Heemstede (NL); Frits Dautzenberg, San Diego, CA (US)

(73) Assignee: Furanix Technologies B.V., Amsterdam (NL)

( * ) Notice: Subject to any disclaimer, the term of this patent is extended or adjusted under 35 U.S.C. 154(b) by 690 days.

(21) Appl. No.: 12/282,288

(22) PCT Filed: Mar. 12, 2007

(86) PCT No.: PCT/EP2007/002146
§ 371 (c)(1),
(2), (4) Date: Dec. 29, 2008

(87) PCT Pub. No.: WO2007/104515
PCT Pub. Date: Sep. 20, 2007

(65) Prior Publication Data
US 2009/0306415 A1    Dec. 10, 2009

(30) Foreign Application Priority Data
Mar. 10, 2006  (EP) ..................................... 06075565

(51) Int. Cl.
*C07D 307/02* (2006.01)
*C10L 1/24* (2006.01)
(52) U.S. Cl. ............. 549/501; 549/500; 44/350; 44/351
(58) Field of Classification Search .................. 549/500, 549/501; 44/350, 351
See application file for complete search history.

(56) References Cited

U.S. PATENT DOCUMENTS
2003/0032819 A1    2/2003  Lightner

FOREIGN PATENT DOCUMENTS
| DE | 3621 517 A1 | 1/1988 |
| DE | 3621517 A1 | 1/1988 |
| GB | 925812 | 5/1963 |
| GB | 00925812 | 5/1963 |

OTHER PUBLICATIONS

Aslam et al, Esterification, 12,4,2000, Kirk-Othermer Encyclopedia of Chemical Technology, vol., 10 ,p. 471-496.*
Fine et al, Chemical Characterization of Fine Particle Emission from Fireplace Combustion of Woods Grown in the Southern United States, 2002, Environmental Science & Technology, 36(7), p. 1442-1451.*
Garves, K., "Acid Catalyzed Degradation of Cellulose in Alcohols", Journal of Wood Chemistry and Technology, vol. 8, No. 1, 121-134 (1988).
Tyrlik, S., et al., "Selective dehydration of glucose to hydroxymethylfurfural and a one-pot synthesis of a 4-acetylbutyrolactone from glucose and trioxane in solutions of aluminium salts", Carbohydrate Research, vol. 315, 268-272, (1999).
Garves, K., "Acid catalyzed degradation of cellulose in alcohols", Journal of Wood Chemistry and Technology, vol. 8 (1), p. 121-134, 1988.
Gandini, A., et al., "Furans in polymer chemistry", Prog. Polym. Sci., XP-002412950, vol. 22, p. 1203-1379, 1997.
Tyrlik, S., et al., "Selective dehydration of glucose to hydroxymethylfurfural and a one-pot synthesis of a 4-acetylbutyrolactone from glucose and trioxane in solutions of aluminum salts", Carbohydrate Research, vol. 315, p. 268-272, 1999.
Gandini, A., et al., "Recent contributions to the preparation of polymers derived from renewable resources", Journal of Polymers and the Environment, XP-002412949, vol. 10, No. 3, p. 105-114, 2002.
Moreau, C., et al., "Recent catalytic advances in the chemistry of substituted furans from carbohydrates and in the ensuing polymers" Topics in Catalysis, vol. 27, Nos. 1-4, p. 11-30, 2004.
European Search Report, Mar. 17, 2009.
Bicker, M. et al. "Dehydration of D-fructose to hydroxymethylfurfural in sub- and supercritical fluids", The Journal of Supercritical Fluids, 36, p. 118-126, Apr. 29, 2005.
B.N Kuznetsov, Rossiiskii khimicheskii zhurnal (Zhurnal Rossiiskogo khimicheskogj obschestva im. D.1. Mendeleeva), 2003, t. XLVII, No. 6, s.83-91. (English translation: B.N Kuznetsov, "Production of liquid fules and their components from woody biomass", Ros. Khim. Zh. (J. of Rus. Mendeleyev Chem. Society), 2003, vol. XLVII, No. 6, pp. 83-91).

* cited by examiner

*Primary Examiner* — Taylor Victor Oh
(74) *Attorney, Agent, or Firm* — Hoffmann & Baron, LLP

(57) ABSTRACT

Method for the manufacture of organic acid esters of 5-hydroxymethylfurfural by reacting a fructose or glucose-containing starting material with an organic acid or its anhydride in the presence of a catalytic or sub-stoechiometric amount of solid acid catalyst. The catalysts are heterogeneous and may be employed in a continuous flow fixed bed reactor. The esters can be applied as a fuel or fuel additive.

17 Claims, No Drawings

METHOD FOR THE SYNTHESIS OF ORGANIC ACID ESTERS OF 5-HYDROXYMETHYLFURFURAL AND THEIR USE

CROSS-REFERENCE TO RELATED APPLICATIONS

This application is the National Stage of International Application No. PCT/EP2007/002146, filed Mar. 12, 2007, which claims the benefit of European Application No. EP 06075565.9, filed Mar. 10, 2006, the contents of which are incorporated by reference herein.

FIELD OF THE INVENTION

The present invention relates to a method for the preparation of derivatives of 5-hydroxymethylfurfural (HMF), in particular ester derivatives of HMF, such as the condensation product of formic acid or its anhydride with HMF (formioxymethylfurfural), acetic acid or its anhydride with HMF (5-acetoxymethylfurfural), or of propionic acid or its anhydride with HMF (5-propionoxymethylfurfural) and to their application as a fuel or fuel additive.

BACKGROUND OF THE INVENTION

The conversion of sugars or sugar (hexoses) containing biomass into more economically useful compounds is of increasing interest. Current fuel activities are mainly directed towards ethanol from sugar/glucose. Typically, sucrose and glucose are fermented into ethanol. One glucose molecule is converted into two molecules of ethanol and two molecules of CO2. This conversion has drawbacks especially in view of atom economy, the low energy density of ethanol (7.7 kWh/kg or 6.1 kWh/L) and its relative low boiling point (78.4 degrees Celsius).

Another application area involves the conversion of sugars such as fructose into HMF in the presence of an acid catalyst has been reported (for example in EP0230250 to Suedzucker or EP0561928 to CEA)). In this case, HMF is obtained as a highly potential starting material for obtaining bio-based monomer such as furandicarboxylic acid which can inter alia be used as an alternative to terephthalic acid as a monomer for polyethylene terephthalate type polyesters (Moreau et. al. in Topics in Catalysis Vol 27, Nos. 1-4, 2004, 11-30 and references cited therein). When under these conditions sucrose or glucose was used as a feed, no conversion to HMF is observed (Moreau et. al. in Topics in Catalysis Vol 27, Nos. 1-4, 2004, p 13, col 2. line 2-3), which is a distinct disadvantage given the low price and abundant availability of sucrose and glucose. Only in the presence of DMSO, DMF and DMA (low HMF yields from glucose: Ishida et. al. Bull. Chem. Soc. Jpn 74 2001, 1145) or in a sub- and supercritical mixture of acetone and water (fructose, glucose, sucrose and inulin conversion to HMF in 77%, 48%, 56% and 78% yields respectively: Vogel et. al. Green Chemistry 5, 2003, 280) reasonable HMF yields from starting materials other than fructose were obtained.

In the current market situation, fructose as feed is undesirable given the high price thereof, compared to glucose and/or sucrose. Therefore, so far, no process for the synthesis of HMF has been developed on an industrial scale.

The synthesis chemistry and applications of HMF are reviewed extensively in Lewkowski, ARKIVOC 2001, (i) 17-54; in Gandini, Prog. Polym. Sci. 22, 1997, 1203; in Lichtenthaler, C. R. Chimie, 7, 2004, 65 and Acc. Chem. Res. 35, 2002, 728; and Moreau, Topics in Catalysis, 27, 2004, 11.

Concluding, the current methods for the synthesis of HMF mostly start from fructose and typically do not give high yield, partly attributable to the instability of HMF under the acidic reaction conditions. In most acid-catalysed water-based reactions, the further reaction to levulinic acid and humins has been reported, making this a less attractive alternative.

The present inventors have set out to overcome these disadvantages.

SUMMARY OF THE INVENTION

Surprisingly, the inventors have found that the conversion of hexose-containing starting material, in particular fructose and/or glucose-containing starting material and more particular glucose-containing material that may be derived from biomass in the presence of a catalytic or sub-stoechiometric amount of acid in the presence of an organic acid or its anhydride with or without the presence of one or more additional diluents leads to the formation of the corresponding organic acid ester of HMF in good yield and selectivity.

DETAILED DESCRIPTION OF PREFERRED EMBODIMENTS

Thus, the invention pertains to a method for the manufacture of organic acid esters of 5-hydroxymethylfurfural by reacting a fructose and/or glucose-containing starting material with an organic acid or its anhydride in the presence of a catalytic or sub-stoechiometric amount of acid catalyst.

It was found that this in situ formation and derivatisation of HMF prevents the occurrence of the onward and undesired reaction towards the above-mentioned levulinic acid and humins, thus leading to an efficient procedure for the conversion of glucose-containing material into HMF derivatives.

In certain embodiments, the organic acid is a mono-carboxylic acid, preferably selected from the group consisting of (un)branched aliphatic acids, (un)branched unsaturated acids, preferably (un)branched aliphatic acids, more preferably C1-C5 (un)branched aliphatic acids, most preferable formic acid, acetic acid, propionic acid, (iso)-butyric acid, particularly preferable formic acid, acetic acid, more particularly preferable acetic acid or the anhydrides thereof, in particular formic anhydride, acetic anhydride, propionic anhydride and (iso)butyric anhydride. Acetic acid or its anhydride is the most preferred acid/anhydride in the method of the present invention as acetic acid or its anhydride can also be derived from biomass.

As these HMF derivatives can now be obtained in high yields, in one step, from very cheap hexose or hexose containing starting materials such as sucrose and glucose, and as furthermore, the acetyl ester (acetoxymethylfurfural) has a high energy content (typically about 8.7 kWh/L, vs 8.8 kWh/L for gasoline and only 6.1 kWh/L for ethanol) and in contrast to HMF is a liquid at room temperature, they can directly be used as a fuel additive as an alternative for MTBE or as a fuel itself. Mixtures of acids and/or anhydrides may also be employed.

The acid catalyst in the method of the present invention can be selected from amongst (halogenated) organic acids, inorganic acids, salts, Lewis acids, ion exchange resins and zeolites or combinations and/or mixtures thereof. In certain embodiments, the pKa of (halogenated) organic acid catalyst is equal or smaller than the pKa of the organic acid or the anhydride. It is thought that typically the stronger acid functions as the catalyst. In certain preferred embodiments, the acid catalyst is a heterogeneous catalyst. In certain embodiments, the acid catalyst is a homogenous catalyst. The acid may be a protonic, Brønsted or, alternatively, a Lewis acid. In certain embodiment, the acid may be a (halogenated) organic or inorganic acid. In certain embodiments, the organic acid can be selected from amongst formic acid, acetic acid, tri (chloro or fluoro)acetic acid, oxalic acid, levulinic acid, maleic acid or para-toluenesulphonic acid. In certain embodiments, the inorganic acid can be selected from amongst phosphoric acid, sulphuric acid, hydrochloric acid, hydrobromic acid, nitric acid, hydroiodic acid, optionally generated in situ. In certain embodiments, the inorganic acid is selected form the group of sulphuric acid, phosphoric acid, hydrochloric acid, nitric acid.

In certain embodiments, the salt can be one of $(NH_4)_2SO_4/SO_3$, ammonium phosphate, triethylamine phosphate, pyridinium salts, pyridinium phosphate, pyridinium hydrochloride/hydrobromide/perbromate, DMAP, aluminium salts, Th and Zr ions, zirconium phosphate, Cr-, Al-, Ti-, Ca-, In-ions, $ZrOCl_2$, $VO(SO_4)_2$, $TiO_2$, V-porphyrine, Zr-, Cr-, Ti-porphyrine. In certain embodiments, the Lewis acid can be one of $ZnCL_2$, $AlCl_3$, $BF_3$. In certain embodiments, the ion exchange resins can be one of Amberlite, Diaion, levatit. In certain embodiments, it is preferred that the acid catalyst is a solid catalyst that may be selected form the group consisting of acid resins, natural clay mineral, zeolites, supported acids such as silica impregnated with mineral acids, heat treated charcoal, metal oxides, metal sulfides, metal salts and mixed oxides and mixtures thereof. In certain embodiments, mixtures or combinations of acid catalysts can be used.

The temperature at which the reaction is performed may vary, but in general it is preferred that the reaction is carried out at a temperature from 50 to 300 degrees Celsius, preferably from 100 to 250, more preferably from 150 to 200 degrees Celsius. In general, temperatures higher than 300 are less preferred as the selectivity of the reaction as many by-products occur, inter alia caramelisation of the sugar. Performing the reaction below the lowest temperature is also less preferable because of the slow reaction speed.

The fructose and/or glucose-containing starting material can be selected from a wide variety of feeds. In general any feed with a sufficient high fructose or glucose content can be used. It is preferred that the glucose-containing starting material is selected from the group of starch, amylose, galactose, cellulose, hemi-cellulose, glucose-containing disaccharides such as sucrose, maltose, cellobiose, lactose, preferably glucose-containing disaccharides, more preferably sucrose or glucose.

The catalyst can be added to the reaction mixture in an amount varying from 0.01 to 40 mole % drawn on the fructose or glucose content of the fructose and/or glucose-containing starting material preferably from 0.1 to 30 mole %, more preferably from 1 to 20 mole %.

In certain embodiments, one or more solvents may be added, in general to aid the dissolution of the glucose containing material or as a diluent. The solvent may be selected form the group consisting of water, sulfoxides, preferably DMSO, ketones, preferably methyl ethylketone, methylisobutylketone, acetone or mixtures of two or more of the above solvents.

In certain embodiments, the ratio of organic acid or anhydride/solvent is from 50 to 0.1, preferably from 20 to 1, more preferably from 10 to 2.

Higher amounts of organic acid or anhydride may have the result that the reaction is too slow due to the limited solubility (hence availability of the glucose containing material), whereas too much solvent in the system may lead to a too high dilution, which in both cases are less preferred results. One of the preferred solvents is water.

In certain embodiments, the method can be performed in a continuous flow process. In such method, homogenous catalysts may be used and the residence time of the reactants in the flow process is between 0.1 second and 10 hours, preferably from 1 second to 5 hours, more preferably from 1 minute to 1 hour.

In certain embodiments, the continuous flow process is a fixed bed continuous flow process or a reactive (catalytic) distillation process with preferably a heterogeneous acid catalyst. To initiate or regenerate the heterogeneous acid catalyst or to improve performance, an inorganic or organic acid may be added to the feed of the fixed bed or reactive distillation continuous flow process. In a fixed bed process, the liquid hourly space velocity (LHSV) can be from 1 to 1000, preferably from 5 to 500, more preferably from 10 to 250 and most preferably from 25 to 100.

As explained above, the application of the products of the method of the present invention, i.e. the esters, is in the use as a fuel or fuel additive and as precursor for the manufacture of 2,5-di(hydroxymethyl)furan, furan-2,5-dicarboxylic acid, 2-hydroxymethylfuran-5-carboxylic acid, 2,5-(dihydroxymethyl)tetrahydrofuran, which can be used as monomers in a polymerisation process, optionally after conversion of the diol to a diamine. See for a review Moreau, Topics in catalysis, 2004, 27, 11-30

EXAMPLE 1

Sucrose Feed, Mineral Acid Catalyst

In a continuous flow reactor, sucrose 10 mmol/l, dissolved in water/acetic acid/10% $H_2SO_4$, was reacted at a temperature of 195 degrees Celsius with a residence time between 6 and 60 seconds and a flow rate of 10 ml/min, i.e. 3.33 ml/min/reactor. At 6 seconds, mainly conversion into fructose and glucose was observed, but at prolonged residence times, 2 main furan peaks were observed in the UV spectrum. Mass spectrometry identified these products as HMF and AMF (5-acetoxymethylfurfural) with a selectivity of >90% at a conversion of 25%.

EXAMPLE 2

Glucose Feed, Mineral Acid Catalyst

In a continuous flow reactor, glucose 10 mmol/l, dissolved in water/acetic acid/10% $H_2SO_4$, was reacted at a temperature of 195 degrees Celsius with a residence time between 6 and 60 seconds and a flow rate of 10 ml/min, i.e. 3.33 ml/min/reactor. At 30 seconds, 2 main furan peaks were observed in the UV spectrum. Mass spectrometry identified these products as HMF and AMF (5-acetoxymethylfurfural) with a selectivity of >90% at a conversion of 10%.

Apparatus

Continuous parallel flow reactor system consisting of four quartz reactors inserted in a silver heating block; temperature and flow regulators and three HPLC pumps. Two of the pumps deliver the liquid to the reactors and third one is employed to dilute the reaction products prior to collection.

Analytical Method

The reaction products were quantified with the aid of HPLC-analysis with an internal standard (saccharine, Sigma Aldrich). A Merck-Hitachi L7000 chromatograph, equipped UV and RI detectors, was used. Stationary phase were reverse phase C18 (Sunfire 3.5 µm, 4.6×100 mm, Waters) and cation exchange (SupelcogelH, 4.6×300 mm, SigmaAldrich) columns connected in series. A gradient elution at a constant flow 0.6 ml/min and temperature 60° C. was used according to the following scheme.

| Time (min) | 0.2% TFA (aq) | Methanol | Acetonitrile |
|---|---|---|---|
| 0 | 90.0 | 7.0 | 3.0 |
| 10 | 90.0 | 7.0 | 3.0 |
| 11 | 80.0 | 0.0 | 20.0 |
| 15 | 80.0 | 0.0 | 20.0 |
| 16 | 90.0 | 7.0 | 3.0 |
| 21 | 90.0 | 7.0 | 3.0 |

General Procedure

A 1.25 wt % solution of glucose (99.7% Sigma Aldrich) in 50% or 90% aqueous acetic acid was flowed through a fixed bed (200 µl) of a heterogeneous catalyst at 180° C. Flow rates were chosen such to achieve a space velocity 0.25 or 0.5 $min^{-1}$, i.e. contact time 2 or 4 min. Liquid coming out of the reactors was diluted by a mixture of water and ethanol (50:50) to prevent tubing blockages.

Catalysts Tested:
Catalyst 1 Zeolite beta SAR25 (CBV Zeolyst)
Catalyst 2 Zeolite Y high SAR (CBV Zeolyst)
Catalyst 5 Mordenite H SAR 90 (CBV Zeolyst)
Catalyst 7 Zeolite Y SAR 5.17 (CBV Zeolyst)
Contact time and space velocity were calculated as follows:

$$Sv = Fr_{feed}/V_{cat}$$

Sv space velocity ($min^{-1}$)
$Fr_{feed}$ flow rate feed (ml/min)/
$V_{cat}$ catalyst volume (ml)

$$t_c = 1/Sv$$

$t_c$ contact time (min)
Conversion of substrate, selectivity and yield of furan derivatives were calculated according to the following formulae:

$$X = 100 * m_{r\ substrate}/m_{0\ substrate}$$

X conversion (%)
$m_{r\ substrate}$ amount of reacted substrate (mg)
$m_{0\ substrate}$ amount of substrate in feed (mg)

$$S_{compound} = 100 * n_{r\ substrate}/n_{0\ substrate}$$

$S_{compound}$ selectivity to compound (%)
$n_{r\ substrate}$ moles of substrate reacted
$n_{0\ substrate}$ moles of substrate in feed $$Yield = 100 * n_{product}/n_{0\ substrate}$$

Yield yield (%)
$n_{product}$ moles of product formed

DATA Fructose + acetic acid with solid acid catalyst 1
fructose conc 55.5 mmol/L; 90% AcOH

| Res time/s | fructose conversion % | Y (HMF) % | Y (AMF) % | S (HMF) % | S (AMF) % |
|---|---|---|---|---|---|
| 10 | 25 | 2 | 5 | 8 | 20 |
| 30 | 50 | 4 | 15 | 8 | 30 |
| 60 | 75 | 7 | 17 | 9 | 23 |
| 120 | 98 | 6 | 20 | 6 | 20 |

DATA Glucose + acetic acid with solid acid catalyst 1
glucose conc 55.5 mmol/L; 90% AcOH

| Res time/s | glucose conversion % | Y (HMF) % | Y (AMF) % | S (HMF) % | S (AMF) % |
|---|---|---|---|---|---|
| 60 | 73 | 2 | 5 | 3 | 7 |
| 180 | 92 | 1 | 6 | 1 | 7 |
| 300 | 97 | 1 | 6 | 1 | 6 |
| 600 | 98 | 1 | 7 | 1 | 7 |

DATA Sucrose + Acetic acid with solid acid catalyst 2
sucrose conc 27.8 mmol/L (55.5 mmol/L C6H12O6); 90% AcOH

| Res time/s | glu + fru conversion % | Y (HMF) % | Y (AMF) % | S (HMF) % | S (AMF) % |
|---|---|---|---|---|---|
| 60 | 86 | 4 | 13 | 5 | 15 |
| 180 | 96 | 3 | 15 | 3 | 16 |
| 300 | 98 | 3 | 17 | 3 | 17 |
| 600 | 99 | 2 | 16 | 2 | 16 |

Engine Test

In a small-scale model diesel engine, comparative testing is performed with normal commercial diesel as a fuel and the same commercial diesel to which samples of 1 wt. %, 2 wt. %, 3 wt. %, 5 wt %, and 10 wt. % HMF or AMF are added, respectively. The diesel samples with HMF are less homogenous on visual inspection (solid particles remain visible, flocculation) and above 5 wt. % HMF, a solid deposit is sometimes observed. AMF is added as a liquid and does not yield any mixing or flocculation problems. The engine is run stationary with a set volume (100 mL) of fuel until empty. HMF containing fuels run less regular, whereas AMF containing fuels run at a regular pace and for a longer period (up to 15%). On visual inspection of the engine, AMF provides less visual contamination.

What is claimed is:

1. A method for the manufacture of esters of a mono-carboxylic acid and 5-hydroxymethylfurfural by reacting a fructose and/or glucose-containing starting material with the mono-carboxylic acid selected from the group consisting of formic acid, acetic acid, propionic acid, butyric acid and isobutyric acid in the presence of a catalytic or sub-stoichiometric amount of acid catalyst, selected from the group consisting of (halogenated) organic acids, inorganic acids, salts, Lewis acids, ion exchange resins, zeolites and combinations thereof;
   wherein water is present as solvent;
   wherein the ratio of organic acid/solvent is from 50 to 0.1; and
   wherein the method is performed in a continuous flow process.

2. The method according to claim 1, wherein the pKa of (halogenated) organic acid catalyst is equal or smaller than the pKa of the organic acid.

3. The method according to claim 1, wherein the acid is a solid Brønsted acid.

4. The method according to claim 1, wherein the acid is a solid Lewis acid.

5. The method according to claim 1, wherein the acid catalyst is selected from the group consisting of sulphuric acid and zeolites.

6. The method according to claim 1, wherein the reaction is performed at a temperature from 150 to 300 degrees Celsius.

7. The method according to claim 1, wherein the fructose and/or glucose-containing starting material is selected from the group of starch, amylose, galactose, cellulose, hemi-cellulose and glucose-containing disaccharides.

8. The method according to claim 1, wherein the residence time in the flow process is between 1 minute to 1 hour.

9. The method according to claim 1, wherein the continuous flow process is a fixed bed continuous flow process.

10. The method according to claim 9, wherein the fixed bed comprises a heterogeneous acid catalyst.

11. The method according to claim 1, wherein the continuous flow process is a reactive distillation or a catalytic distillation process.

12. The method according to claim 9, wherein in addition to a heterogeneous acid catalyst, an inorganic or (halogenated) organic acid catalyst is added to the feed of the fixed bed or catalytic distillation continuous flow process.

13. The method according to claim 12, wherein the LHSV is from 1 to 1000.

14. The method according to claim 7, wherein the fructose and/or glucose-containing starting material is sucrose or glucose.

15. A diesel fuel comprising an ester of 5-hydroxymethyl furfural and a mono-carboxylic acid selected from the group consisting of formic acid, acetic acid, propionic acid, butyric acid and isobutyric acid, as manufactured with the method according to claim 1.

16. The method according to claim 11, wherein in addition to a heterogeneous acid catalyst, an inorganic or (halogenated) organic acid catalyst is added to the feed of the fixed bed or catalytic distillation continuous flow process.

17. The method according to claim 1, wherein the mono-carboxylic acid is acetic acid.

* * * * *